United States Patent
Sgourakes et al.

[11] Patent Number: 5,641,270
[45] Date of Patent: Jun. 24, 1997

[54] DURABLE HIGH-PRECISION MAGNETOSTRICTIVE PUMP

[75] Inventors: George E. Sgourakes, Millis; Joseph F. Actor, Uxbridge; Richard L. Vigeant, East Douglas; Carlton H. Paul, Groton, all of Mass.

[73] Assignee: Waters Investments Limited, Wilmington, Del.

[21] Appl. No.: 509,472

[22] Filed: Jul. 31, 1995

[51] Int. Cl.⁶ .......................... F04B 49/06; F04B 17/00; F04B 35/00
[52] U.S. Cl. ................. 417/44.2; 417/322; 417/385; 417/389; 417/473
[58] Field of Search ........................ 417/1, 5, 7, 8, 417/18, 21, 44.2, 245, 246, 322, 385, 389, 472, 473

[56] References Cited

U.S. PATENT DOCUMENTS

| | | | |
|---|---|---|---|
| 3,406,670 | 10/1968 | Hines | 417/322 |
| 4,056,095 | 11/1977 | Rey et al. | 417/389 |
| 4,265,600 | 5/1981 | Mandroian | 417/379 |
| 4,483,665 | 11/1984 | Hauser | 417/401 |
| 4,585,397 | 4/1986 | Crawford et al. | 417/412 |
| 4,804,314 | 2/1989 | Cusack | 417/322 |
| 4,828,464 | 5/1989 | Maier et al. | 417/385 |
| 4,917,575 | 4/1990 | Miller, Jr. et al. | 417/52 |
| 5,249,929 | 10/1993 | Miller, Jr. et al. | 417/379 |
| 5,286,176 | 2/1994 | Bonin | 417/322 |

FOREIGN PATENT DOCUMENTS

| | | |
|---|---|---|
| 4032555-A1 | 4/1992 | Germany. |
| 4204435-A1 | 8/1993 | Germany. |

Primary Examiner—Timothy Thorpe
Assistant Examiner—Xuan M. Thai
Attorney, Agent, or Firm—Anthony J. Janiuk

[57] ABSTRACT

A magnetostrictive pump is provided which makes use of a magnetostrictive element which, when an alternating magnetic field is applied to it, compresses a chamber containing a working fluid. A bellows located within the working fluid is repeatedly compressed by the compression of the chamber, and pumps a fluid to be pumped in and out of the bellows. Since the magnetostrictive element does not directly contact the bellows, the bellows life is greatly extended. Valves are provided to direct the fluid flow in a desired manner. The pump may be combined with other pumps in various series or parallel arrangements to create a pump system. The pump may be pre-biased to make its response more linear by either mechanical or magnetic biasing. A permanent magnet may be used to magnetically bias the pump and create an "at-rest" initial extension of the magnetostrictive element. Similarly, a spring may be used to mechanically load the magnetostrictive element. A controller is used to detect feedback signals from pressure and pump displacement transducers, and thereby provide active control of the pump or pump system. It is especially useful for high performance liquid chromatography.

19 Claims, 6 Drawing Sheets

DURABLE HIGH-PRECISION MAGNETOSTRICTIVE PUMP

BACKGROUND OF THE INVENTION

1. Field of the Invention

This invention relates to a novel magnetostrictive pumps capable of delivering precise quantities of fluids. In particular, a magnetostrictive pump adapted for fluid delivery for high performance liquid chromatography is described.

2. Description of the Related Art

Magnetostrictive materials are those which are deformed under the influence of a magnetic field. Many magnetostrictive materials are known such as those described in European Patent Appl. No. 92300980.7, which is incorporated herein by reference. A magnetostrictive material which is commercially available is Terfenol-D®,which is an alloy containing iron and the rare earth metals terbium and dysprosium, and which has the stoichiometric composition, $Tb_xDy_{1-x}Fe_{1.9-1.98}$ This material is available from Etrema Corporation, Ames, Iowa. Terfenol-D® typically is characterized by a magnetostrictive effect which is two orders of magnitude greater than materials which are conventional and not "giant" magnetostrictive such as Terfenol-D®.

At the present time, magnetostrictive pumps exist which are utilized to pump fluids. U.S. Pat. No. 4,726,741 discloses a magnetostrictive pump including a magnetostrictive element in direct communication with a portion of a pump cylinder containing a fluid to be pumped. Magnetically controlled valves are utilized to control the direction of fluid flow in response to movement of the magnetostrictive material. Sealing means such as "O" rings are provided between the magnetostrictive material and the housing for the magnetostrictive material.

U.S. Pat. Nos. 4,795,317 and 4,795,318 disclose magnetostrictive pumps wherein the magnetostrictive element directly contacts a fluid within a portion of a pump cylinder which fluid is to be pumped under the influence of the moving magnetostrictive material. These pumps also include a sealing means between the magnetostrictive material and the housing for the magnetostrictive material.

German patent application DE 4204435 A1 discloses a magnetostrictive pump utilizing a magnetostrictive element which is in direct contact with a flexible membrane which, in turn, contacts a fluid to be pumped. German patent application DE 4032555 A1 discloses a magnetostrictive pump utilizing a magnetostrictive element which directly contacts a diaphragm in the shape of a bellows. The bellows encloses a fluid to be pumped under the force exerted by the magnetostrictive element.

Magnetostrictive pumps utilizing a magnetostrictive element which directly contacts a fluid to be pumped are undesirable since such pumps require a sealing means between the magnetostrictive material and the housing containing the magnetostrictive material in order to prevent fluid by-pass between the magnetostrictive element and the housing. These seals rapidly deteriorate under the force exerted by the reciprocating magnetostrictive element. Magnetostrictive pumps constructed so that the magnetostrictive element directly contacts a diaphragm are undesirable since the materials normally utilized to form the diaphragm have limited mechanical strength and fail within a relatively short time due to fatigue and corrosion.

High performance liquid chromatography (HPLC) is a process wherein a sample is separated into its individual constituents by passing the sample through a column of material, usually particles, which functions to separate the sample constituents within the column. The sample is delivered to the column with a pump which has a very stable flow rate. Pressures, between about 50 psi and 6000 psi are common with a flow rate typically between 1 microliters per minute and 5 milliliters per minute. This flow rate is usually programmable and is as free of pulsations as possible. At the present time, there is no available pumping system which can achieve the full range of these pressures and flow rates with a single pump design that satisfies the stability and accuracy requirements.

Conventional liquid chromatography (LC) pumps typically are based on the use of reciprocating pistons driven by means of electric motors (usually stepping motors) leveraged through a gear train or cams. The forces inherent in the electric motors are modest, and extensive gearing is essential in order to attain the desired high pressures. Generally, two identical reciprocating pump heads are required for steady flow. The pump heads are run out of phase with each other so that one is pumping liquid while the other is refilling with liquid to be pumped. In the motor-driven pumps, the switchover between heads usually results in pressure transients of approximately 300 psi. Furthermore, seals surrounding the sliding pistons reduce the reliability of reciprocating pumps because they wear and occasionally shed particles of material into the sample fluid stream, causing malfunctions of check valves and a requirement for larger capillary tubing within the system to prevent clogging due to the particles.

Another category of presently available pumps are diaphragm pumps. These pumps have flexible "bellows" driven with electric motors by a mechanism of cams, and have the same problems of pulsation as the reciprocating pumps. These diaphragm pumps operate with a shorter stroke than reciprocating pumps, and those presently available do not attain the high pressures provided by reciprocating piston pumps due to the lack of available force of present drive mechanisms. However, diaphragm pumps are generally regarded as being more reliable, since they do not require the seals used by piston pumps.

Accordingly, it would highly desirable to provide a magnetostrictive pump and pump system which does not require seals between adjacent moving and static parts, and which is capable of generating high pressure within a wide pressure range, and maintaining precise flow rates. Furthermore, it would be desirable to provide such a pump and pump system which is capable of reliably withstanding the force and pressure changes normally encountered in HPLC procedures for long periods of reliable operation.

SUMMARY OF THE INVENTION

In accordance with this invention, a pump and pump system are provided with a magnetostrictive element which, when extended, cooperates with a chamber containing a working fluid to pressurize the working fluid. The increased pressure of the working fluid causes a compression of a bellows structure which is substantially surrounded by the working fluid. When the magnetostrictive element is retracted, the bellows structure decompresses, returning to its original shape.

The bellows structure is in fluid communication with a fluid inlet and a fluid outlet through which fluid is conducted into and out of the bellows. The bellows is otherwise fluid tight such that the fluid pumped into and out of the bellows is sealed from the working fluid. During pumping, the magnetostrictive element does not directly contact the bellows but contacts a compliant surface of the chamber either directly or indirectly via a solid extension element which is secured to a working end of the magnetostrictive element. A stationary end (relative to the housing) of the magnetostrictive element is opposite the working end, and is secured to the housing. As the position of the working fluid chamber is also fixed relative to the housing, the expansion and contraction of the magnetostrictive element creates the desired pressure changes in the chamber.

In one embodiment of the invention, a pump system is provided comprising a plurality of pumps, preferably two pumps, each comprising a magnetostrictive element and coil, a housing, a working fluid chamber and a bellows, as described above. The pumps may be arranged in series or in parallel. A controller, such as a digital signal processor, is provided which regulates the current through each pump coil to optimally control the pumping. The pump thus effects extremely stable and precise flow rates and pressures, minimizing flow rate and pressure transients in the fluid being pumped. Detectors which monitor the output pressure of the pumping system, the differential pressure between the working fluid chambers of the two pumps, and the displacement of the working end of the magnetostrictive element may be used. The detection signals from these detectors are input to the controller, and used to modify the coil currents to best optimize the pumping action of the pump system.

In one variation of the invention, a pump uses a magnetostrictive element that is provided with a bias which shifts its magnetostrictive response characteristic, such that an "at-rest" position of the magnetostrictive material is located on a more linear region of the magnetostrictive response curve. The biasing reduces the power consumption of the pump, and simplifies control by operating within a more linear range of magnetostrictive response. The bias may be provided by a permanent magnet, such as a magnetic sheath surrounding the electromagnetic coil, or by an electromagnet having a coil that surrounds the pump driving coil. Alternatively, the bias may be established mechanically with a spring that compresses the magnetostrictive element, so as to establish a mechanical stress that shifts the magnetostrictive response curve.

When the bias is established magnetically, an initial "at-rest" pressure on the compliant surface of the working fluid chamber results and, consequently, produces an "at-rest" pressure on the working fluid and the bellows. Unlike the non-biased or the spring-biased pump embodiments, the coils of which are driven by a varying, but unidirectional current, the magnetically-biased pump is driven by an alternating current which fluctuates between positive and negative values. Thus, as the pump is driven, the pressure on the working fluid fluctuates above and below the "at-rest" pressure.

The use of magnetostrictive elements to indirectly drive a bellows of a pump permits precise control of the pump due to the instant response capability and lack of hysteresis common in prior art pumps. The magnetostrictive drive element requires no mechanical leverage to achieve large forces and responds directly to electrical control signals used to generate a driving magnetic field. The short stroke of the magnetostrictive pump is particular suitable for highly accurate measurement by a variety of available position detectors so that the resulting fluid displacement of the bellows can be determined in real time. In addition, since the bellows does not contact the magnetostrictive element, and the bellows does not support the pressure of the liquid being pumped, the life of the bellows is greatly extended.

DETAILED DESCRIPTION OF THE PREFERRED EMBODIMENTS

In accordance with this invention, a pump is provided which utilizes a magnetostrictive element and a working fluid chamber. The chamber has a compliant surface which is contacted by an extension that moves with a working end of the magnetostrictive element. Contained within the chamber is a working fluid and a bellows which is surrounded by the working fluid. The bellows defines a volume into and out of which flows a fluid to be pumped. The fluid to be pumped is isolated from the working fluid by the walls of the bellows. As described in more detail hereinafter, a plurality of these pumps may be arranged to work in concert with one another as part of a pump system.

A controller which controls the generation of a magnetic field to drive the magnetostrictive element can be provided to regulate flow rate and pressure of the fluid to be pumped. The controller is preferably a high speed controller, such as a digital signal processor (DSP), that digitizes an analog input signal, performs calculations on the digitized input and transforms the result into output signals which are used to drive the pump coil (or coils). The performance of the DSP may be modified in response to a number of monitored parameters such as the displacement of the working end of the magnetostrictive element (or elements), the output fluid pressure of the pump (or pumps), or a differential pressure between a plurality of pumps. By monitoring inputs such as these as a function of time, the controller may responsively modify the coil driving signal (or signals) to attain the desired pressure and flow rate characteristics in the fluid being pumped.

Figure 1:
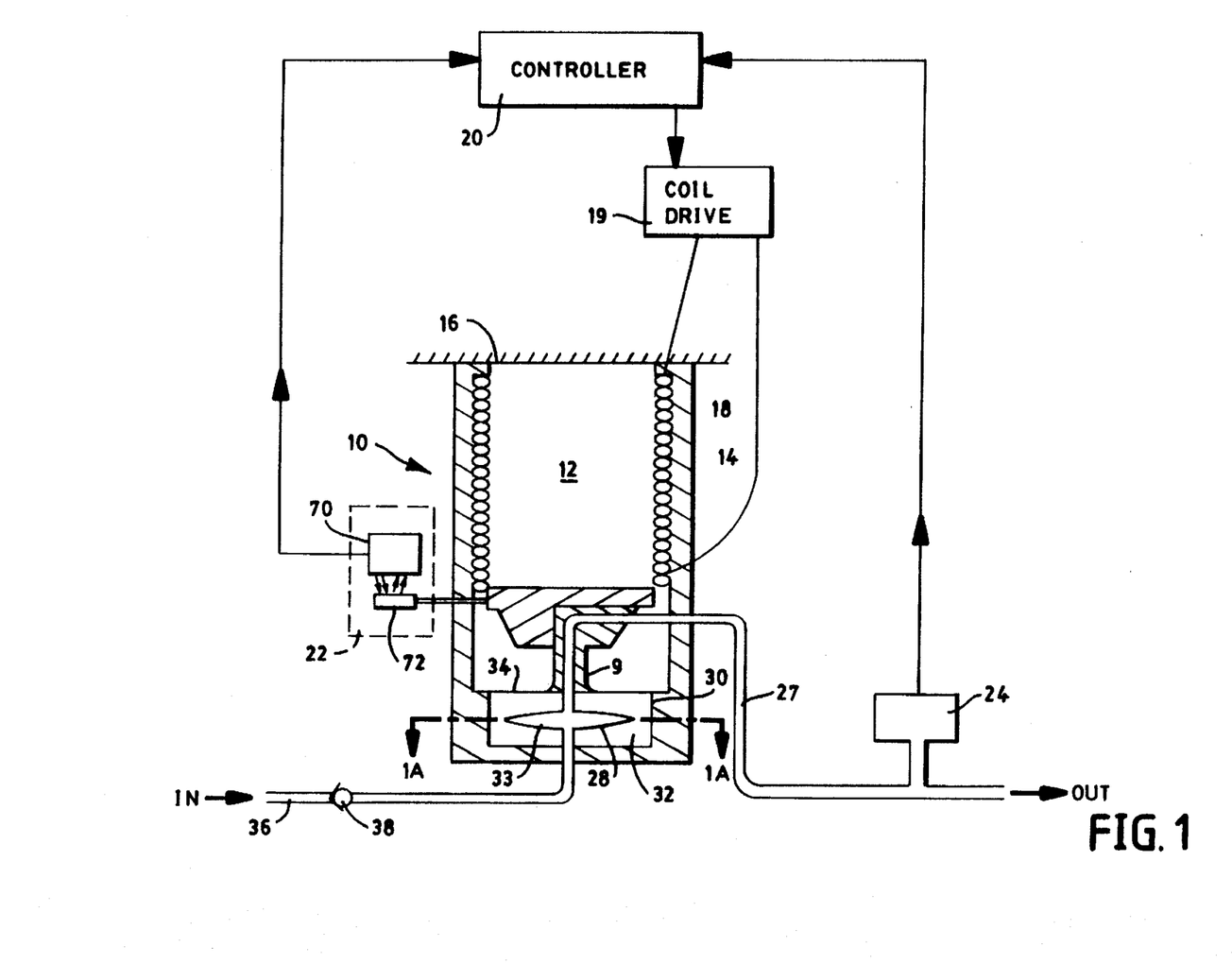
FIG. 1 is a cross-sectional schematic view of a magnetostrictive pump according to the invention.

Referring to the cross-sectional schematic view of FIG. 1, a pump 10 according to the invention includes a magnetostrictive element 12 which is positioned within housing 14 and which is fixed at one end 16 by any convenient means. A magnetic field-generating coil 18 surrounds magnetostrictive element 12. The coil 18 is powered by a coil drive circuit 19, which drives a current through the coil 18 in response to an input from a controller 20. The controller 20 can be electronically connected to a displacement sensor 22 and/or an output pressure transducer 24, which is positioned at fluid outlet conduit 27.

A bellows 28 comprising a flexible material is positioned within a chamber 30 which contains a working fluid 32. The magnetostrictive element 12 is positioned within coil 18 with its "working end" adjacent a flexible top surface 34 of chamber 30. The magnetostrictive element 12 is rigidly connected (directly or indirectly) to an extension 9 which contacts the surface 34, so that the driving of the magnetostrictive element 12 causes a corresponding deflection of the surface 34. This deflection changes the pressure of the working fluid 32 within chamber 30 as a function of the displacement of the extension 9. An increase in working fluid pressure, in turn, increases the pressure on bellows 28, such that fluid within the bellows is pumped out through outlet conduit 27.

As the bellows is compressed, fluid is forced out through outlet conduit 27. An intake valve 38 (preferably a low-volume ball check valve) located in inlet conduit 36 is biased toward the bellows 28, and therefore does not allow fluid being pumped to pass into intake conduit 36. The ball check valve 38 is selected such that the relative amount of fluid displaced by the stroke of the ball in the valve is significantly less than the total fluid quantity pumped on each stroke of the pump. This ensures that fluid is pumped, and that it does not merely reciprocate the ball within the valve.

The magnetostrictive element has a typical stroke of about 0.001 inches per inch of length and is capable of being controlled within a millionth of an inch. The magnetostrictive response of the magnetostrictive element 12 is virtually instantaneous (microseconds). In addition, the diameter of the extension 9 which contacts surface 34 is relatively large, typically between about 0.5 and about one inch. When the magnetostrictive element expands under the influence of the magnetic field induced by the coil 18, it is capable of providing a large pressure, typically, up to about 6000 psi or more. A preferred material for surface 34 is Carpenter 450 Alloy available from Carpenter Technology Corporation. This alloy is capable of withstanding stress imposed by a magnetostrictive element at a stroke of about 0.005 inch for ten years or greater.

As shown in the embodiment of FIG. 1, pressure transducer 24 outputs a signal to controller 20 in response to the pressure in outlet conduit 27. The transducer 24 could alternatively be located in chamber 30. However, it then decreases the fluid volume of the chamber 30, and correspondingly reduces the pumped fluid volume.

The absolute displacement of the working end of the magnetostrictive element 12 is also preferably monitored. This is accomplished using a displacement sensor which monitors either the magnetostrictive element 12 itself, or extension 9 which moves with the working end of the magnetostrictive element 12. In the embodiment of FIG. 1 a conventional photodetector 22 is used which includes a photosensor 70 which outputs an optical signal that is reflected by a reflective surface 72 attached to the extension 9. As the position of the reflective surface changes relative to the photosensor 70, the magnitude of the reflected optical signal that is detected by the photosensor 70 changes. As this magnitude changes, the output signal from the photosensor 70 to the controller 20 changes correspondingly, and indicates the relative displacement of the working end of the magnetostrictive element.

Knowledge of both the displacement (i.e. bellows stroke) and the fluid pressure at all times during the pump cycle allows for a real time calculation of the fluid compressibility. This calculation is useful for maintaining a constant flow rate within the system as the load on the system changes, such as when viscosity changes cause changes in back pressure. Thus, the pump 10 provides extremely precise flow rates at levels far below that available with present pump technology. Exemplary flow rates are as low as a fraction of a microliter per minute, with a precision of ±0.0001. This level of precision can be maintained over the entire range of operation because it derives from the resolution of the feedback detectors and/or transducers rather than from the mechanical design of the pump.

Figure 1A:
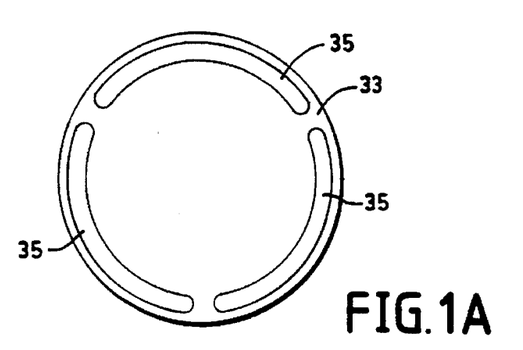
FIG. 1A is an isolated view of a baffle located within the bellows of a magnetostrictive pump according to the present invention.

FIG. 1A is a sectional view of a baffle 33 located within the working fluid chamber 30. The baffle has slots 35 along its outer edge. The fluid being pumped must pass through the slots as it moves through the bellows 28. The positioning of the slots near the outer edge of the baffle 33 forces the fluid to follow a path through the bellows 28 which ensures the purging of the bellows. If the baffle was not present, fluid might pass directly through the center of the bellows 28 without forcing residual fluid out of regions away from the center of the bellows. Thus, the baffle promotes proper purging of the bellows such that, if the fluid being pumped is changed, the new fluid is not contaminated by residual fluid left over from a previous pumping operation.

Figure 2:
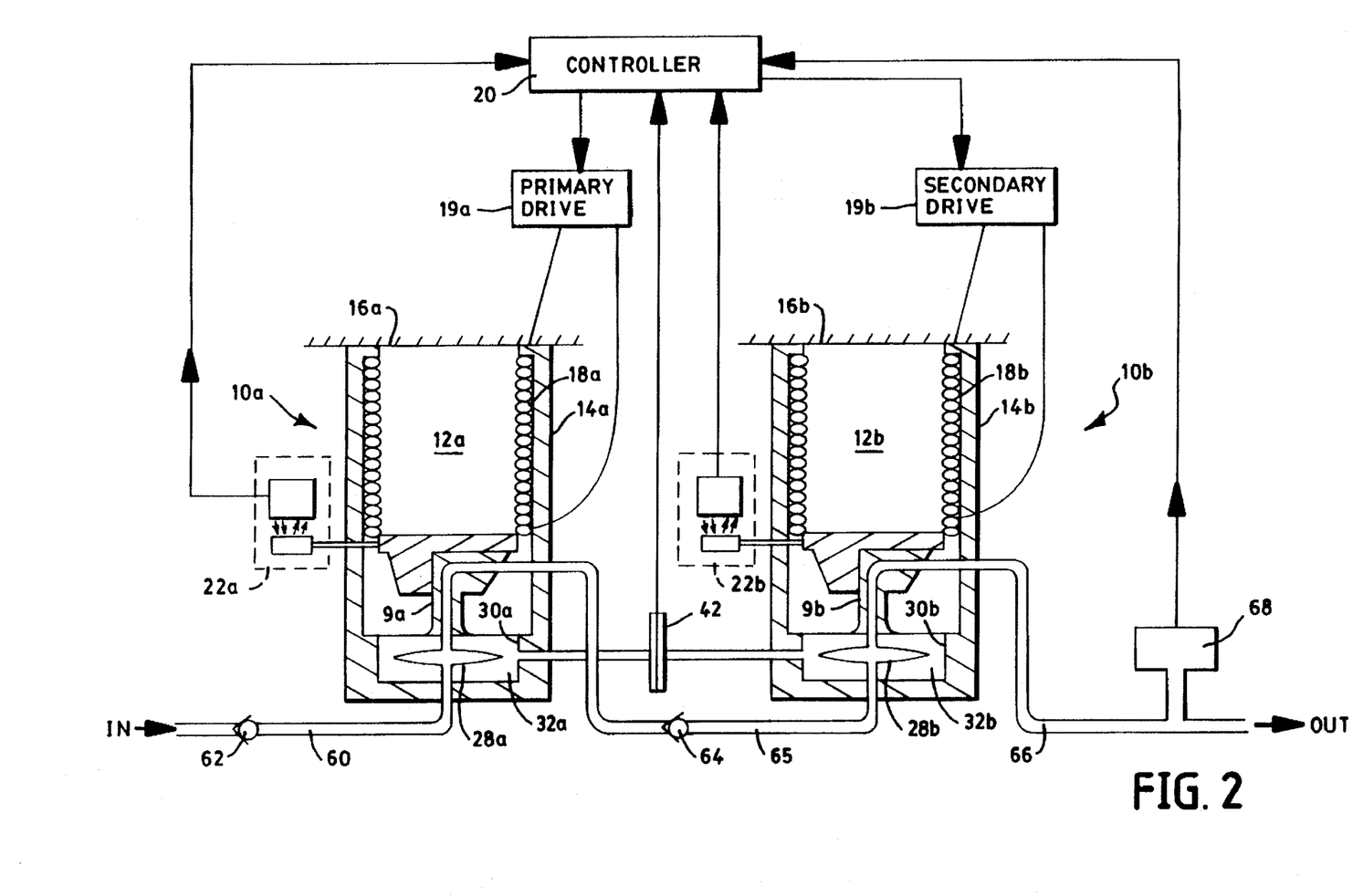
FIG. 2 is a cross-sectional schematic view of a pump system according to the invention wherein two pumps are arranged in series relationship.

Referring to FIG. 2, a pump system is shown which uses a series arrangement of two pumps. Elements of each pump of FIG. 2 which are the same as those of the pump of FIG. 1 are identified by the same reference numbers as used in FIG. 1, but are supplemented with the designations "a" and "b", where specific to one of the respective pumps 10a or 10b of the pump system.

In the pump system of FIG. 2, the fluid to be pumped passes through inlet check valve 62 and fluid inlet conduit 60, where it is pumped by means of pump 10a into and out of bellows 28a. The fluid pumped out of pump 10a passes through check valve 64, which is located in interconnection conduit 65. Of this pumped fluid, a portion of it refills a bellows 28b of pump 10b which is being driven on a refill stroke, and the remainder is forced out through outlet conduit 66. Bellows 28b is preferably significantly smaller than bellows 28a (one-half the volume in the preferred embodiment) and is therefore filled by only a portion of the fluid pumped by primary pump 10a. This results in a significant amount of fluid being pumped out of the pump system during the pumping stroke of pump 10a. Alternatively, the pumps could be the same size and operate at different rates. The pumping strokes of the two pumps 10a, 10b are out of phase with each other, such that the pumping stroke of secondary pump 10b begins when the pumping stroke of primary pump 10a ends. During its pumping stroke, pump 10b forces out fluid with which it was filled by the pumping stroke of pump 10a. Since check valve 64 is reverse-biased relative to pump 10b, the fluid is forced out through outlet conduit 66. During the pumping stroke of pump 10b, pump 10a is on a refill stroke, and is drawing fluid into bellows 28a via inlet conduit 60.

The pumping strokes of pumps 10a, 10b are controlled by controller 20, which modifies the signals driving the coils of the two pumps in response to an input signal from outlet pressure transducer 68. While this is the minimum control signal input required by the controller, it is also desirable to have other feedback signals as well. In the preferred embodiment, a differential pressure transducer 42 is provided which outputs a signal to the controller indicative of the pressure differential between the working fluid in the chambers 30a, 30b of pumps 10a and 10b. Alternatively, the differential pressure could be sensed between inlet conduit 60 and interconnection conduit 65. Two displacement sensors 22a, 22b, each like that shown in FIG. 1, are also provided, and each provides a signal to controller 20 indicative of the position of its respective extension 9a, 9b.

The controller 20 controls the current to the two coils by outputting control signals to primary drive circuit 19a and secondary drive circuit 19b. The drive circuits 19a, 19b are current drivers of conventional design, and each modifies the current to its respective coil in response to the state of the signal it receives from controller 20. By monitoring the changes in signals input to it from sensors 68, 22a, 22b and 42, the controller 20 can modify its signals to drive circuits 19a, 19b so as to achieve the desired output, typically a precise flow rate with minimal variations in pressure. In general, the controller 20 controls the drive circuits 19a, 19b so as to produce a stable output flow rate from the pumping system. In the preferred embodiment, the primary pump 10a is the master, and the stroke of the secondary pump 10b is controlled to complement the primary. For example, the secondary pump is controlled by controller 20 via secondary drive circuit 19b to begin its pumping stroke when the primary pump stroke is complete (subject to a slight overlap of the pumping strokes to minimize output pressure fall off). The secondary pump then pumps until the primary has refilled its bellows, and pre-pressurized the fluid in anticipation of another pumping stroke. Once the primary bellows is pre-pressurized, the secondary pump is controlled by the controller 20 via secondary drive circuit 19b to discontinue its pumping stroke.

The use of differential pressure transducer 42 provides a simple means by which to trigger the reversal of the stroke of secondary pump 10b. When the differential pressure has been a non-zero value, and goes to zero, the controller can determine that the primary pump 10a has fully pre-pressurized, and can initiate the primary pump stroke while simultaneously reversing the stroke of the secondary pump 10b to allow the secondary pump bellows 28b to refill. This coordination of the two pump strokes can be maintained very precisely, so as to minimize pressure transients at the pumping stroke "switchover" from pump 10a to pump 10b.

The point of equal pressure between the two pump chambers 30a, 30b also provides a means by which to calculate the compressibility of the fluid being pumped. In gradient chromatography, the fluid mixture being pumped changes with time. Usually, the fluids being mixed have different compressibilities and, therefore, as the mixture changes, so does the overall compressibility of the fluid being pumped. Since the displacement (i.e. stroke) of the primary pump 10a is known to the controller, the compressibility of the fluid may be ascertained from the known volume change of the fluid being pumped and the pressure reached at full pressurization. Thus, the relative mixing of fluids may be tracked by tracking a change of fluid compressibility.

The manner in which the controller 20 responds to various inputs from the sensors 68, 22a, 22b and 42 to modify the pumping strokes of pumps 10a, 10b depends on the desired output characteristics of the pumping system (i.e. flow rate, flow rate stability, output pressure, output pressure stability). In the preferred embodiment, the controller comprises a digital signal processor (DSP) which maintains a look-up table of various signal values which are output in response to any of a plurality of possible expected inputs. While the different possible methods of control in this respect are numerous and detailed, one example is demonstrated by the response characteristic depicted in FIGS. 4A and 4B.

Figure 4A:
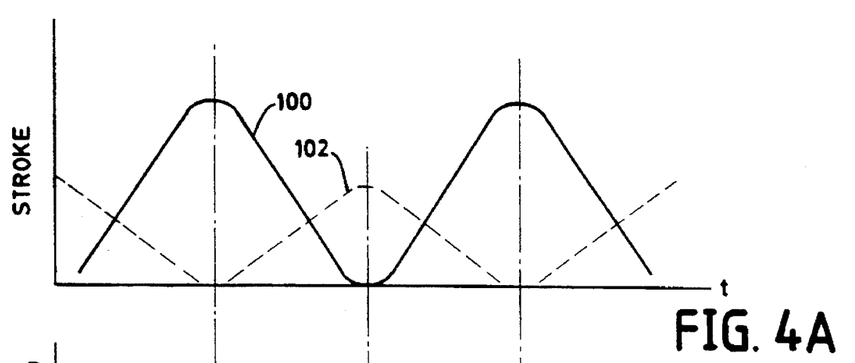
FIG. 4A is a graph of the pump stroke of a first pump and a second pump of a pump system versus time.
Figure 4B:
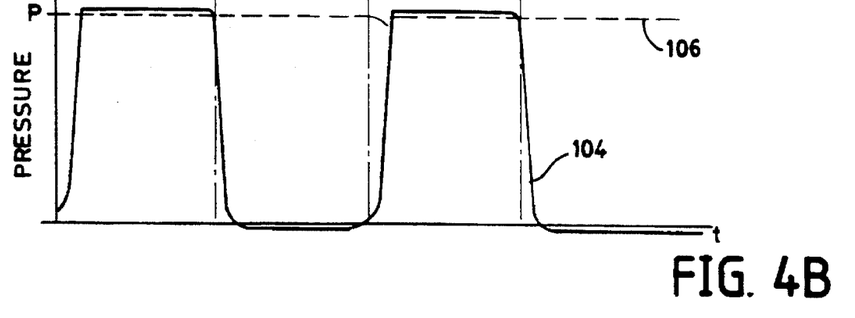
FIG. 4B is a graph of the output pressure of a first pump and a second pump of a pump system versus time.

FIGS. 4A and 4B demonstrate a desired response characteristic for a two-stage, series magnetostrictive pump system optimized for a stable output pressure. FIG. 4A depicts the stroke of the two pump stages versus time (the primary pump stroke being represented by solid line 100 and the secondary pump stroke being represented by dashed line 102). FIG. 4B depicts the output pressure of each of the two pump stages versus time (the primary pump pressure being represented by solid line 104 and secondary pump pressure being represented by dashed line 106. The time axes of FIGS. 4A and 4B are aligned to show the correlation between the pressure and stroke curves. The controller 20 (via drive circuits 19a, 19b) controls the magnitude, frequency and phase of the currents through the pump coils to best approximate a desired output pressure P.

As shown in FIG. 4A, the strokes 100 (primary), 102 (secondary) of the two pump stages (assuming ideal conditions) are 180 degrees out of phase with each other. Furthermore, the stroke of the secondary pump stage has a peak magnitude of about 50% of the peak magnitude of the primary stage. Referring to FIG. 4B, the pressure of the primary pump (solid line 104) is a high positive pressure (approximately the output pressure P) during the pumping stroke of the primary pump, and is slightly negative during the refill stroke of the primary pump, as the pump draws new fluid into bellows 28a. The pressure of the secondary pump (dashed line 106), which is also equal to the output pressure of the pump system, is relatively stable at desired pressure P. During a refill stroke of the secondary pump, the output pressure is maintained by the primary pump which is forcing fluid into bellows 28b and through output port 66. A slight pressure drop may exist during the transition from the secondary pumping stroke to the primary pumping stroke, due to the time lag of check valve 64.

To provide proper feedback control of the system, the controller 20 makes use of the signal from the output pressure transducer 68, and may use signals from displacement sensors 22a, 22b and differential pressure transducer 42. There exist a number of different ways to program the controller (e.g. set up the look-up table of the DSP) to responsively control the output pressure, and any of these programming tasks are well within the abilities of those skilled in the art, given the graphical depiction of FIGS. 4A and 4B. For example, given a drop in overall output pressure, the controller might respond by increasing the magnitude of the stroke of both pumps. In the case of a periodic fluctuation of the output pressure, the controller 20 might adjust the phase of one of the two pumps to smooth the output. The controller 20 might also have inputs from displacement sensors for the two extensions 9a, 9b, and therefore have feedback information on the correlation between the current through a particular coil and the response of the magnetostrictive element. In addition, differential pressure 42 might be included, and would provide the controller 20 with information on the relative pressure of the two pumps.

Figure 3:
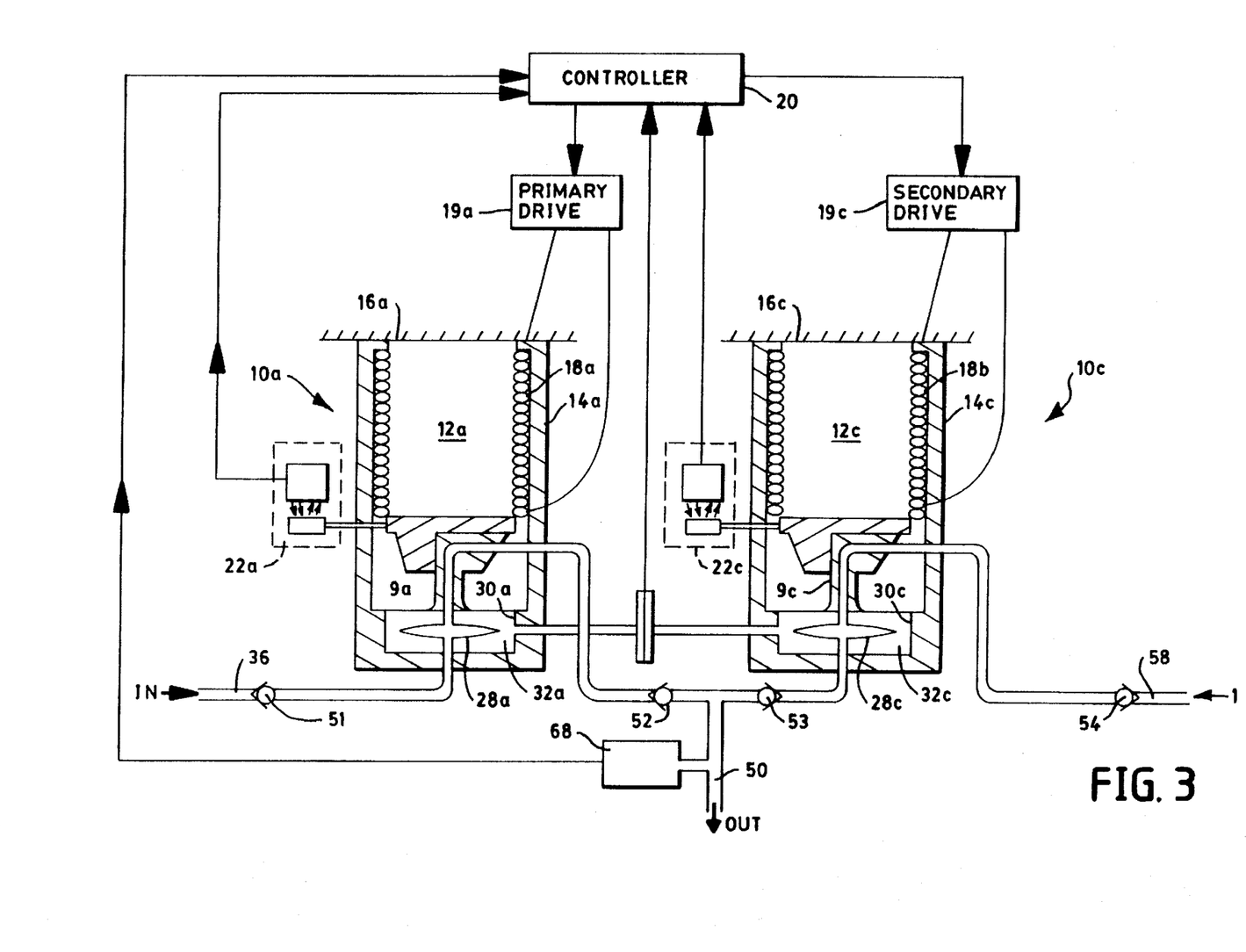
FIG. 3 is a cross-sectional schematic view of a pump system of this invention wherein two pumps are arranged in a parallel relationship.

Shown in FIG. 3 is an alternative pump system which uses two pump stages in a parallel arrangement. Because the first stage of the pump system is essentially identical to the primary stage of the series pump system of FIG. 2, the same reference numerals are used for this pump stage as were used in FIG. 2. Elements of the second stage of the parallel pump of FIG. 3 use similar numbers as the secondary stage of FIG. 2, but are identified by the designation "c".

The pump system of FIG. 3 comprises two pumps, pump 10a and pump 10c, which are controlled to operate in tandem to deliver a constant flow rate at a constant pressure. In general, when magnetostrictive element 12a of pump 10a is contracting, magnetostrictive element 12c of pump 10c is expanding, so that flow through fluid outlet 50 remains constant at a constant pressure. Check valves 51, 52, 53 and 54 are positioned so that fluid flow passes from fluid inlet conduits 36 and 58 into bellows 28a, 28c of pumps 10a, 10c, respectively, and out through fluid outlet 50. An output pressure transducer 68 provides an output signal to controller 20 to allow proper feedback control.

Because the two pumps 10a, 10c of FIG. 3 function in parallel, the bellows 28a, 28c of the pumps 10a, 10c preferably both define the same volume. Thus, pump 10a and pump 10c each displace the same amount of fluid with each pumping stroke. The controller 20 controls the electrical current delivered to the coils 18a, 18c via primary drive circuit 19a and secondary drive circuit 19. By controlling the stroke of each pump such that the pumps alternate pumping strokes (with some slight overlap of the pump strokes in time to minimize output pressure drop-off), a constant output pressure and flow rate is maintained. As with the series pump embodiment of FIG. 2, the controller may receive inputs from any or all of output pressure transducer 68, differential pressure transducer 42 and displacement sensors 22a, 22b. These inputs are used to monitor the pumping operation, and to correct or customize it by modifying the control of the pumps 10a, 10c in response to the inputs.

The linearity of the pump response to drive currents and the rate of the response to these drive currents is improved if the operating point of the magnetostrictive element is modified. Two biasing means are shown herein. The optimization of the linearity and the rate of response can be achieved by applying a magnetic field or a mechanical strain to the magnetostrictive element. The magnetic field can be produced by a permanent magnet or an electromagnetic coil.

Figure 5:
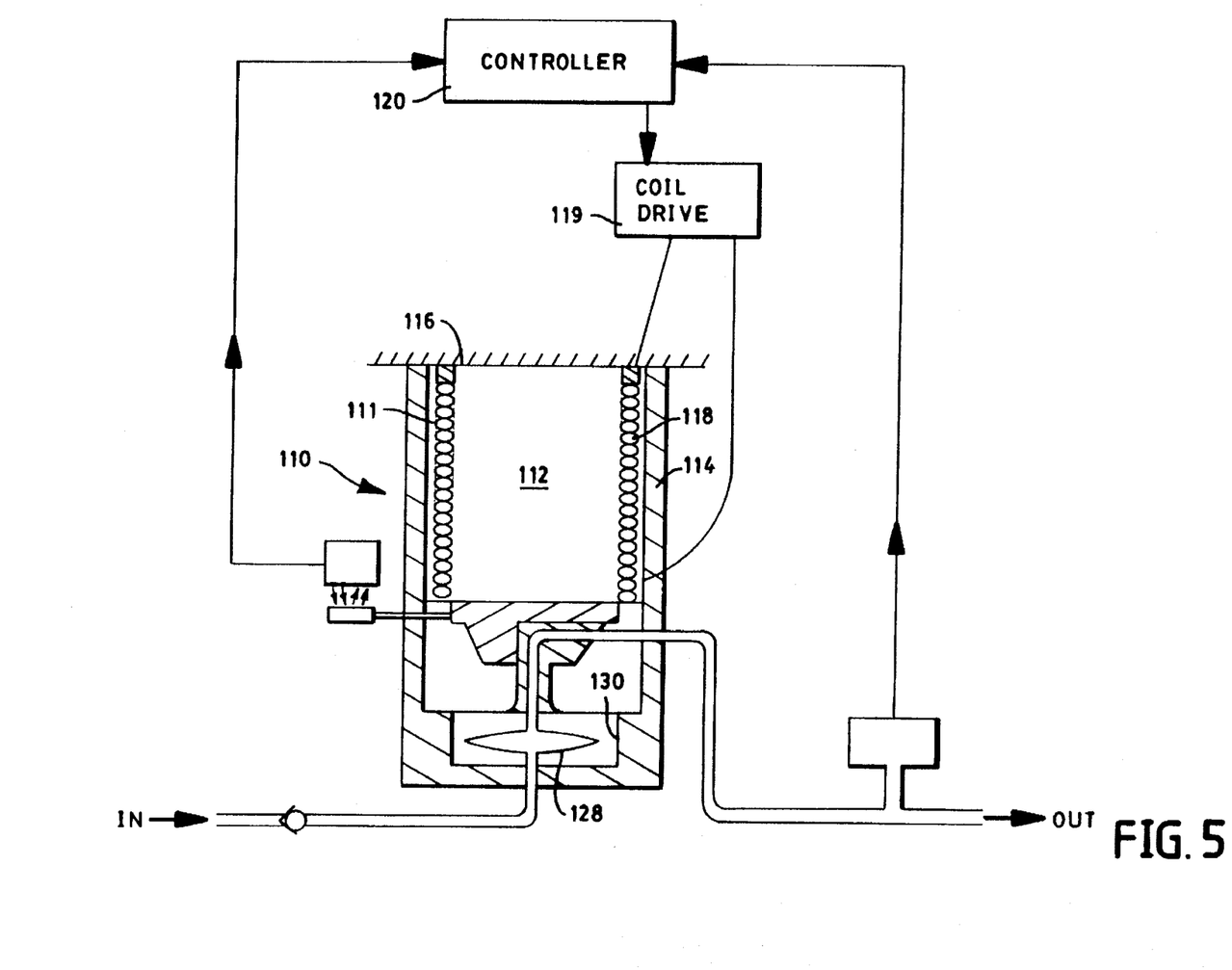
FIG. 5 is a cross sectional schematic view of an alternative embodiment of the pump of FIG. 1 in which the magnetostrictive element is magnetically-biased.

An embodiment using a magnetic bias is shown in FIG. 5 and is applicable to each of the pump arrangements of the present invention. Pump 110 is similar to pump 10 of FIG. 1, but has a permanent magnet 111 located in housing 114 which surrounds coil 118. The permanent magnet 111 could be placed outside the coil 118, or interleaved with coil 118, in order to obtain the greatest efficiency of using the magnetic field of the coil 118 to alternately cancel or add to the magnetic field of the permanent magnet 111 which acts on the magnetostrictive element. In the preferred embodiment, the permanent magnet 111 is shaped like a hollow cylinder, and provides a magnetic bias to magnetostrictive element 112. The bias is in the direction of the pumping stroke of the pump, such that the pump is normally applying a positive pressure to chamber 130. This, in turn, partially activates the magnetostrictive element such that it has a mid-stroke position at rest.

Coil drive circuit 119 is also similar to the coil drive circuit of FIG. 1 but, in response to control signals from controller 120, drives the coil 118 with an alternating current which alternates between positive and negative magnitudes. Thus, while the current driving the coil 118 is positive, the electromagnetically-generated field from coil 118 adds to the field generated by the permanent magnet 111, and while the current driving the coil 118 is negative, the electromagnetically-generated field counteracts the field of the permanent magnet 111. While the pumping action in this embodiment is the same as in the embodiment of FIG. 1, the use of the magnetic bias requires less power to drive the magnetostrictive element. The response of the magnetostrictive element to the electromagnetic field is more linear in the range over which this pump must be driven, as compared to that of FIG. 1. The magnetically-biased pump may be used in place of any of the non-biased pumps of the present invention, with appropriate accommodations being made for the necessary range of positive and negative drive currents.

Figure 6:
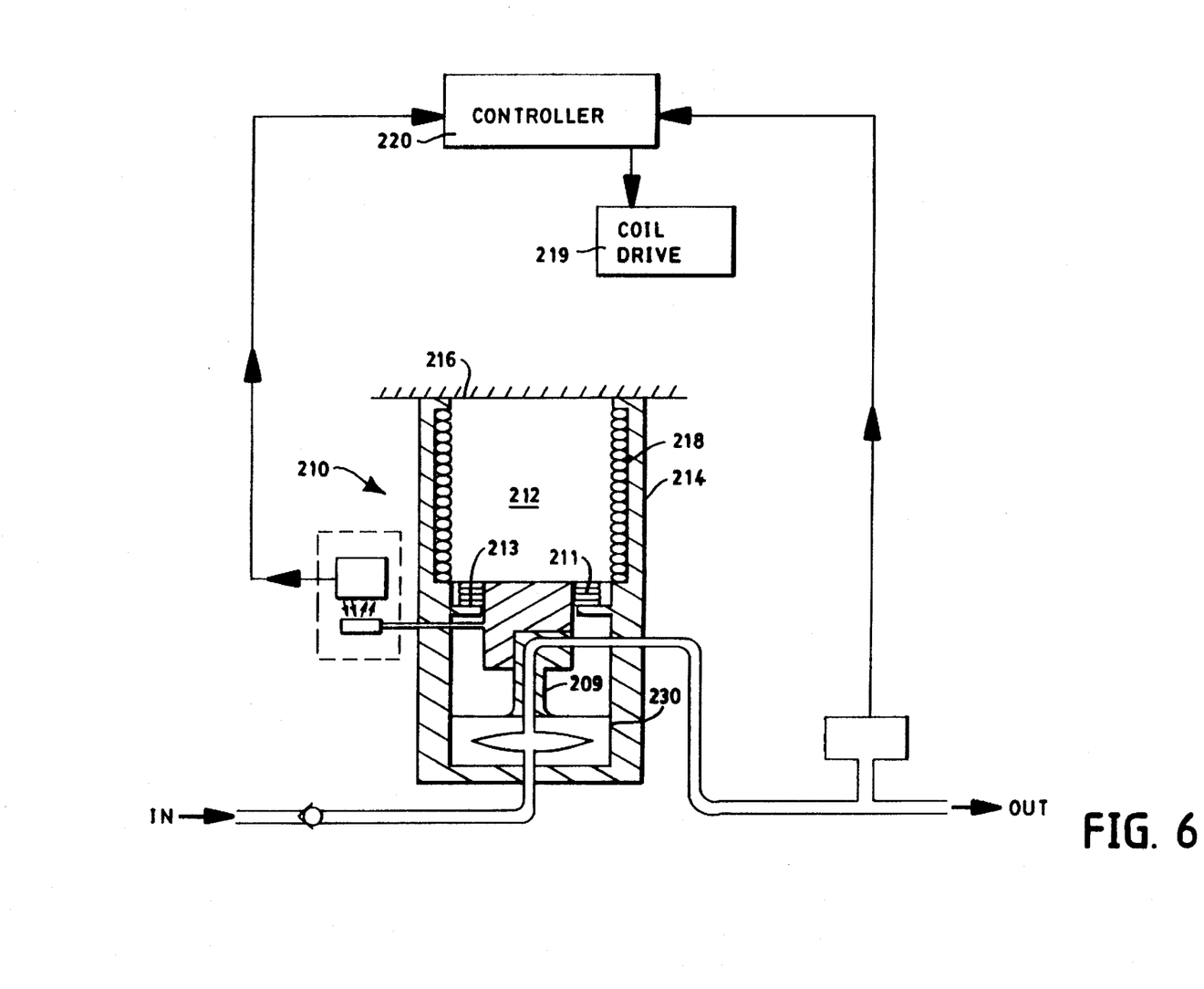
FIG. 6 is a cross sectional schematic view of an alternative embodiment of the pump of FIG. 1 in which the magnetostrictive element is spring-biased.

Still another alternative embodiment is shown in FIG. 6, and is similar to the embodiment of FIG. 5 in that it provides the magnetostrictive element with an initial bias. In this embodiment, however, the bias on magnetostrictive element 212 is provided by a coil spring 211 which physically compresses the magnetostrictive material. The spring 211 is mounted on a lip 213 of the housing 214, which extends further inward than the rest of the housing. This lip 213 provides a surface which is parallel to the working end of the magnetostrictive element 212, and the spring 211 is compressed between the magnetostrictive element 212 and the lip 213. As shown, the extension 209 is shaped somewhat differently than the extension 9 of FIG. 1 so as to accommodate the lip 213.

The compression of the magnetostrictive element 212 provides an initial bias to the response of the magnetostrictive material. In other words, the response characteristic (i.e. a graphical plot of the expansion of the magnetostrictive material versus the magnetic field applied) is shifted relative to the expansion axis. This shift results in a more linear portion of the response characteristic being located in the operating range of the pump 210. However, in the embodiment of FIG. 6, there is no initial "at-rest" compression of the working fluid chamber 230. Thus, it is not necessary that the current from coil drive circuit 219 switch between positive and negative polarities. A positive current is sufficient to drive the coil 218.

While the invention has been shown and described with regard to a preferred embodiment thereof, those skilled in the art will recognize that various changes may be made in form and detail without departing from the spirit and scope of the invention as defined by the appended claims.

What is claimed is:

1. A fluid pump comprising:
    a magnetostrictive element having a first end and a second end opposite the first end;
    an electromagnetic field generator in proximity to the magnetostrictive element which generates and imposes a varying magnetic field upon the magnetostrictive element to vary a length of said magnetostrictive element between said first end and said second end in response to a drive signal;
    a fluid-tight chamber containing a working fluid and having a compliant surface located proximate to one end of said element, the compliant surface being deflected by a change in said length of the magnetostrictive element so as to change the pressure of the working fluid;
    a flexible bellows substantially encompassed by the chamber and substantially surrounded by the working fluid, the bellows defining a variable interior volume isolated from the working fluid, the volume varying in response to the urgings of one end of the element;
    a fluid supply conduit through which fluid is introduced from a fluid source to the interior volume of the bellows;
    a fluid outlet conduit through which fluid is transferred from the bellows to an output of the pump; and
    a valve for preventing fluid backflow from the bellows to the supply conduit.

2. A fluid pump according to claim 1 further comprising a means for biasing said length of the magnetostrictive element by a predetermined amount.

3. A fluid pump according to claim 1 further comprising:
    an outlet pressure sensor which is responsive to a fluid pressure in the outlet conduit and which generates a pressure signal indicative thereof; and
    a controller for generating the drive signal, the controller detecting the pressure signal and modifying the drive signal in response thereto.

4. A fluid pump according to claim 1 further comprising:

a displacement sensor which is responsive to a change in said length of the magnetostrictive element, and which generates a displacement signal indicative thereof; and a controller for generating the drive signal, the controller detecting the displacement signal and modifying the drive signal in response thereto.

5. A fluid pumping system comprising:

a first pump comprising a first magnetostrictive element having a length, a first electromagnetic field generator which generates a magnetic field to vary said length of the first magnetostrictive element in response to a first drive signal, a first fluid-tight chamber containing a working fluid and having a compliant surface which is deflected by a change in said length of the first magnetostrictive element so as to change the pressure of the working fluid of the first chamber, and a first flexible bellows substantially encompassed by the first chamber and substantially surrounded by the working fluid of the first chamber;

a second pump comprising a second magnetostrictive element having a length, a second electromagnetic field generator which generates a magnetic field to vary said length of the second magnetostrictive in response to a second drive signal, a second fluid-tight chamber containing a working fluid and having a compliant surface which is deflected by a change in said length of the second magnetostrictive element so as to change the pressure of the working fluid of the second chamber, and a second flexible bellows substantially encompassed by the second chamber and substantially surrounded by the working fluid of the second chamber;

a fluid supply conduit providing fluid communication between a fluid source and the first bellows;

a fluid transfer conduit providing fluid communication between the first bellows and the second bellows;

a fluid outlet conduit providing fluid communication between the second bellows and an output of the pump;

a first valve preventing fluid flow from the first bellows to the supply conduit; and a second valve preventing fluid flow from the second bellows to the first bellows.

6. A fluid pumping system according to claim 5 further comprising a controller for generating the first drive signal and the second drive signal.

7. A fluid pumping system according to claim 6 further comprising a pressure sensor which is responsive to a fluid pressure in the outlet conduit and generates a pressure signal indicative thereof, and wherein the pressure signal is input to the controller and the controller modifies at least one of the drive signals in response thereto.

8. A fluid pumping system according to claim 6 further comprising a differential pressure sensor which is responsive to a difference between a fluid pressure within the first fluid-tight chamber and a fluid pressure within the second fluid-tight chamber, the differential pressure sensor generating a pressure signal indicative of said pressure difference, and wherein the pressure signal is input to the controller and the controller modifies at least one of the drive signals in response thereto.

9. A fluid pumping system according to claim 6 further comprising:

a first displacement sensor responsive to a change in said length of the first magnetostrictive element and generating a first displacement signal indicative thereof, a second displacement sensor responsive to a change in said length of the second magnetostrictive element and generating a second displacement signal indicative thereof, and wherein the first displacement signal and the second displacement signal are input to the controller and the controller modifies at least one of the drive signals in response to at least one of the first displacement signal and the second displacement signal.

10. A fluid pumping system according to claim 5 further comprising means for biasing said length of the first magnetostrictive element by a predetermined amount.

11. A fluid pumping system according to claim 5 further comprising a means for biasing said length of the second magnetostrictive element by a predetermined amount.

12. A fluid pumping system comprising:

a first pump comprising a first magnetostrictive element having a length, a first electromagnetic field generator which generates a magnetic field to vary said length of the first magnetostrictive element in response to a first drive signal, a first fluid-tight chamber containing a working fluid and having a compliant surface which is deflected by an increase in said length of the first magnetostrictive element so as pressurize the working fluid, and a first flexible bellows substantially encompassed by the first chamber and substantially surrounded by the working fluid;

a second pump comprising a second magnetostrictive element having a length, a second electromagnetic field generator which generates a magnetic field to vary said length of the second magnetostrictive in response to a drive signal, a second fluid-tight chamber containing a working fluid and having a compliant surface which is deflected by an increase in said length of the second magnetostrictive element so as pressurize the working fluid of the second chamber, and a second flexible bellows substantially encompassed by the chamber and substantially surrounded by the working fluid of the second chamber;

a first fluid supply conduit providing fluid communication between a first fluid source and the first bellows;

a second fluid supply conduit providing fluid communication between a second fluid source and the second bellows;

a fluid outlet conduit providing fluid communication between the first bellows and the output of the pump and between the second bellows and the output of the pump;

a first valve preventing fluid flow from the first bellows to the first supply conduit; and a second valve preventing fluid flow from the second bellows to the second supply conduit.

13. A fluid pumping system according to claim 12 further comprising:

a third valve preventing fluid flow from the first bellows to the second bellows; and a fourth valve preventing fluid flow from the second bellows to the first bellows.

14. A fluid pumping system according to claim 12 further comprising a controller for generating the first drive signal and the second drive signal.

15. A fluid pumping system according to claim 14 further comprising an pressure sensor which is responsive to a fluid pressure in the outlet conduit and which generates a pressure signal indicative thereof, and wherein the pressure signal is input to the controller and the controller modifies at least one of the drive signals in response thereto.

16. A fluid pumping system according to claim 14 further comprising a differential pressure sensor which is responsive to a difference between a fluid pressure within the first fluid-tight chamber and a fluid pressure within the second fluid-tight chamber, the differential pressure sensor generating a pressure signal indicative of said pressure difference, and wherein the pressure signal is input to the controller and the controller modifies at least one of the drive signals in response thereto.

17. A fluid pumping system according to claim 14 further comprising:

a first displacement sensor responsive to a change in said length of the first magnetostrictive element and generating a first displacement signal indicative thereof;

a second displacement sensor responsive to a change in said length of the second magnetostrictive element and generating a second displacement signal indicative thereof; and wherein the first displacement signal and the second displacement signal are input to the controller and the controller modifies at least one of the drive signals in response to at least one of the first displacement signal and the second displacement signal.

18. A fluid pumping system according to claim 12 further comprising a means for biasing said length of the first magnetostrictive element by a predetermined amount.

19. A fluid pumping system according to claim 12 further comprising a means for biasing said length of the second magnetostrictive element by a predetermined amount.

* * * * *